United States Patent
Panesar et al.

(10) Patent No.: US 12,233,219 B2
(45) Date of Patent: Feb. 25, 2025

(54) METHODS OF MAKING SLEEVED AND PACKAGED HYDROPHILIC CATHETER ASSEMBLIES

(71) Applicant: Hollister Incorporated, Libertyville, IL (US)

(72) Inventors: Satwinder S. Panesar, Foxford (IE); David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 218 days.

(21) Appl. No.: 17/773,760

(22) PCT Filed: Nov. 6, 2020

(86) PCT No.: PCT/US2020/059421
§ 371 (c)(1),
(2) Date: May 2, 2022

(87) PCT Pub. No.: WO2021/092388
PCT Pub. Date: May 14, 2021

(65) Prior Publication Data
US 2023/0001132 A1     Jan. 5, 2023

Related U.S. Application Data

(60) Provisional application No. 62/932,979, filed on Nov. 8, 2019.

(51) Int. Cl.
*A61M 25/00* (2006.01)
*B65B 5/04* (2006.01)
*B65B 55/22* (2006.01)

(52) U.S. Cl.
CPC ...... *A61M 25/002* (2013.01); *A61M 25/0009* (2013.01); *A61M 25/0017* (2013.01); *B65B 5/04* (2013.01); *B65B 55/22* (2013.01); *A61M 2205/02* (2013.01)

(58) Field of Classification Search
CPC ............ A61M 25/002; A61M 25/0009; A61M 25/0017; B65B 5/02
See application file for complete search history.

(56) References Cited

U.S. PATENT DOCUMENTS

| 3,035,691 | A | * | 5/1962 | Rasmussen | ......... A61M 25/002 206/484 |
| 3,817,248 | A | * | 6/1974 | Buckles | .................... A61F 6/14 424/430 |
| 4,026,296 | A | | 5/1977 | Stoy et al. | |

(Continued)

FOREIGN PATENT DOCUMENTS

| CN | 103301551 A | 9/2013 |
| EP | 1131112 B1 | 2/2003 |

(Continued)

OTHER PUBLICATIONS

International Search Report and Written Opinion for International Application No. PCT/US2020/059421 Dated Mar. 12, 2021.

(Continued)

*Primary Examiner* — Lucas E. A. Palmer
(74) *Attorney, Agent, or Firm* — Cook Alex Ltd.

(57) ABSTRACT

Methods of making sleeved and packaged hydrophilic urinary catheters (10).

19 Claims, 4 Drawing Sheets

(56) References Cited

U.S. PATENT DOCUMENTS

| | | | |
|---|---|---|---|
| 4,136,681 A * | 1/1979 | Hon | A61B 5/035 600/561 |
| 4,906,237 A | 3/1990 | Johansson et al. | |
| 5,328,848 A * | 7/1994 | Fong | A61B 50/30 436/16 |
| 5,562,652 A | 10/1996 | Davis | |
| 5,576,072 A | 11/1996 | Hostettler et al. | |
| 5,616,119 A | 4/1997 | Davis | |
| 5,876,663 A | 3/1999 | Laroussi | |
| 5,895,374 A * | 4/1999 | Rødsten | A61M 25/002 206/364 |
| 6,120,904 A | 9/2000 | Hostettler et al. | |
| 6,270,902 B1 | 8/2001 | Tedeschi et al. | |
| 6,528,544 B2 | 3/2003 | Stern et al. | |
| 6,629,961 B1 | 10/2003 | Israelsson et al. | |
| 6,634,498 B2 | 10/2003 | Kayeroed et al. | |
| 6,848,574 B1 | 2/2005 | Israelsson et al. | |
| 6,923,936 B2 | 8/2005 | Swanson et al. | |
| 6,986,868 B2 | 1/2006 | Madsen | |
| 7,022,651 B1 | 4/2006 | Lightcap, Jr. et al. | |
| 7,066,912 B2 | 6/2006 | Nestenborg et al. | |
| 7,282,165 B2 | 10/2007 | Williams, III et al. | |
| 7,334,679 B2 * | 2/2008 | Givens, Jr. | A61M 25/002 206/364 |
| 7,476,223 B2 | 1/2009 | McBride | |
| 7,569,155 B2 | 8/2009 | Schaefer | |
| 7,770,726 B2 * | 8/2010 | Murray | B65D 51/00 604/265 |
| 7,833,475 B2 | 11/2010 | Madsen | |
| 8,133,435 B2 | 3/2012 | Reynolds et al. | |
| 8,177,774 B2 | 5/2012 | House | |
| 8,267,919 B2 | 9/2012 | Utas et al. | |
| 8,608,689 B2 | 12/2013 | Scheller et al. | |
| 8,703,048 B2 | 4/2014 | Nielsen et al. | |
| 8,747,882 B2 | 6/2014 | Utas et al. | |
| 8,747,911 B2 | 6/2014 | Gupta et al. | |
| 8,871,869 B2 | 10/2014 | Dias et al. | |
| 8,998,882 B2 | 4/2015 | Knapp et al. | |
| 9,028,858 B2 | 5/2015 | Nielsen et al. | |
| 9,138,510 B2 | 9/2015 | Madsen | |
| 9,192,741 B1 | 11/2015 | Najibi | |
| 9,220,866 B2 | 12/2015 | Van Groningen et al. | |
| 9,408,946 B2 | 8/2016 | Utas et al. | |
| 9,610,384 B2 | 4/2017 | Belt et al. | |
| 9,801,979 B2 | 10/2017 | Utas et al. | |
| 9,872,970 B2 | 1/2018 | Schønfeldt | |
| 10,112,031 B2 | 10/2018 | Matthiassen | |
| 10,245,355 B2 | 4/2019 | Ingber et al. | |
| 10,293,136 B2 * | 5/2019 | Palmer | A61M 25/002 |
| 10,398,161 B2 | 9/2019 | Arne et al. | |
| 10,561,817 B2 | 2/2020 | Hannon et al. | |
| 10,987,487 B1 * | 4/2021 | Palmer | A61M 25/01 |
| 2001/0001443 A1 * | 5/2001 | Kayerod | A61M 25/002 206/364 |
| 2002/0026182 A1 * | 2/2002 | Joye | A61B 18/02 606/23 |
| 2002/0045049 A1 | 4/2002 | Madsen | |
| 2002/0120333 A1 | 8/2002 | Keogh et al. | |
| 2003/0065292 A1 | 4/2003 | Darouiche et al. | |
| 2003/0124080 A1 | 7/2003 | Kawam et al. | |
| 2003/0219475 A1 | 11/2003 | Truong-Le | |
| 2004/0060260 A1 * | 4/2004 | Gottlieb | A61L 2/26 53/445 |
| 2004/0074794 A1 | 4/2004 | Conway et al. | |
| 2004/0256264 A1 | 12/2004 | Israelsson et al. | |
| 2005/0015076 A1 | 1/2005 | Giebmeyer et al. | |
| 2005/0043715 A1 * | 2/2005 | Nestenborg | A61M 25/002 206/439 |
| 2005/0055044 A1 | 3/2005 | Kangas | |
| 2005/0061698 A1 * | 3/2005 | Delaney | A61M 25/002 206/364 |
| 2005/0109648 A1 * | 5/2005 | Kerzman | A61M 25/0111 206/364 |
| 2005/0137582 A1 | 6/2005 | Kull-Osterlin et al. | |
| 2005/0214376 A1 | 9/2005 | Faure et al. | |
| 2006/0095015 A1 * | 5/2006 | Hobbs | A61M 25/007 604/537 |
| 2006/0155250 A1 * | 7/2006 | Endo | A61M 1/285 604/29 |
| 2006/0163097 A1 * | 7/2006 | Murray | A61M 25/0017 206/364 |
| 2006/0196783 A1 * | 9/2006 | Bruun | A61M 25/0111 206/207 |
| 2006/0263404 A1 * | 11/2006 | Nielsen | A61L 29/085 424/422 |
| 2007/0239107 A1 | 10/2007 | Lundberg et al. | |
| 2007/0244449 A1 | 10/2007 | Najafi et al. | |
| 2008/0142038 A1 | 6/2008 | Kunzler et al. | |
| 2009/0012208 A1 | 1/2009 | Madsen et al. | |
| 2009/0041727 A1 | 2/2009 | Suzuki et al. | |
| 2009/0171317 A1 | 7/2009 | Versi | |
| 2009/0221989 A1 | 9/2009 | Najafi et al. | |
| 2009/0240214 A1 | 9/2009 | Conway et al. | |
| 2010/0166809 A1 | 7/2010 | Northey et al. | |
| 2010/0215643 A1 | 8/2010 | Clevenger et al. | |
| 2010/0258568 A1 | 10/2010 | Frederiksen et al. | |
| 2011/0114520 A1 | 5/2011 | Matthison-Hansen | |
| 2011/0150961 A1 | 6/2011 | Perry et al. | |
| 2012/0207853 A1 | 8/2012 | Alimi et al. | |
| 2012/0289942 A1 | 11/2012 | Becker et al. | |
| 2012/0316515 A1 | 12/2012 | Terry | |
| 2014/0190846 A1 | 7/2014 | Belt | |
| 2014/0271351 A1 | 9/2014 | Nielsen et al. | |
| 2015/0065998 A1 | 3/2015 | Nielsen et al. | |
| 2015/0105756 A1 * | 4/2015 | O'Brien | B65B 7/02 29/428 |
| 2015/0238726 A1 | 8/2015 | Terry | |
| 2015/0264935 A1 | 9/2015 | Chang | |
| 2015/0265801 A1 * | 9/2015 | Rostami | A61M 25/002 206/438 |
| 2015/0273180 A1 * | 10/2015 | Schønfeldt | B65B 55/22 53/413 |
| 2015/0306342 A1 * | 10/2015 | Rostami | A61M 25/0045 604/544 |
| 2016/0129219 A1 * | 5/2016 | Gustavsson | B65B 53/02 53/111 R |
| 2016/0143944 A1 | 5/2016 | Panicheva et al. | |
| 2016/0213880 A1 | 7/2016 | Oflynn et al. | |
| 2017/0296609 A1 | 10/2017 | Ellington et al. | |
| 2017/0312484 A1 | 11/2017 | Shipley et al. | |
| 2017/0326334 A1 * | 11/2017 | Terry | B65D 65/38 |
| 2018/0000993 A1 | 1/2018 | Zhang | |
| 2018/0010038 A1 | 1/2018 | Greenhill-Hooper et al. | |
| 2018/0021481 A1 * | 1/2018 | Yin | A61M 25/002 206/364 |
| 2018/0221541 A1 | 8/2018 | Pesika et al. | |
| 2018/0258363 A1 | 9/2018 | Rhodes et al. | |
| 2019/0001098 A1 | 1/2019 | Utas et al. | |
| 2019/0083746 A1 | 3/2019 | Murray et al. | |
| 2019/0151610 A1 | 5/2019 | Fletter | |
| 2019/0167849 A1 | 6/2019 | McBurney et al. | |
| 2019/0216985 A1 | 7/2019 | McBurney et al. | |
| 2019/0262647 A1 | 8/2019 | Havelka-Rivard et al. | |
| 2019/0290806 A1 | 9/2019 | Farrell et al. | |
| 2020/0038535 A1 | 2/2020 | Montes De Oca et al. | |
| 2020/0054795 A1 | 2/2020 | Farrell et al. | |
| 2020/0146871 A1 | 5/2020 | Palmer | |
| 2020/0155261 A1 * | 5/2020 | O'Flynn | B65D 75/326 |
| 2021/0059654 A1 * | 3/2021 | Ryan | C08L 5/08 |
| 2021/0138189 A1 * | 5/2021 | Montes de Oca | A61M 25/0017 |
| 2021/0260332 A1 * | 8/2021 | Panesar | A61M 25/0009 |
| 2022/0280751 A1 * | 9/2022 | Farrell | A61M 25/01 |
| 2022/0387673 A1 * | 12/2022 | Farrell | A61L 29/16 |
| 2023/0293849 A1 * | 9/2023 | Hughett, Sr. | A61M 25/002 604/544 |

FOREIGN PATENT DOCUMENTS

| | | |
|---|---|---|
| EP | 1312385 B1 | 2/2006 |
| EP | 1312385 B2 | 10/2009 |
| EP | 1714665 B1 | 8/2011 |

(56) References Cited

FOREIGN PATENT DOCUMENTS

| EP | 2423127 A1 | 2/2012 |
| EP | 2468346 A1 | 6/2012 |
| EP | 2695636 A1 | 2/2014 |
| EP | 2550030 B1 | 4/2018 |
| EP | 3071249 B1 | 8/2018 |
| WO | 2002100455 A2 | 12/2002 |
| WO | 2005117914 A2 | 12/2005 |
| WO | 2014/074141 A1 | 5/2014 |
| WO | 2016033234 A1 | 3/2016 |
| WO | 2017001830 A1 | 1/2017 |
| WO | 2018028831 A1 | 2/2018 |
| WO | 2018029279 A1 | 2/2018 |

OTHER PUBLICATIONS

Castro, et al. "Natural deep eutectic systems as alternative nontoxic cryoprotective agents", Cryobiology, 83, 1-12 (2018).

* cited by examiner

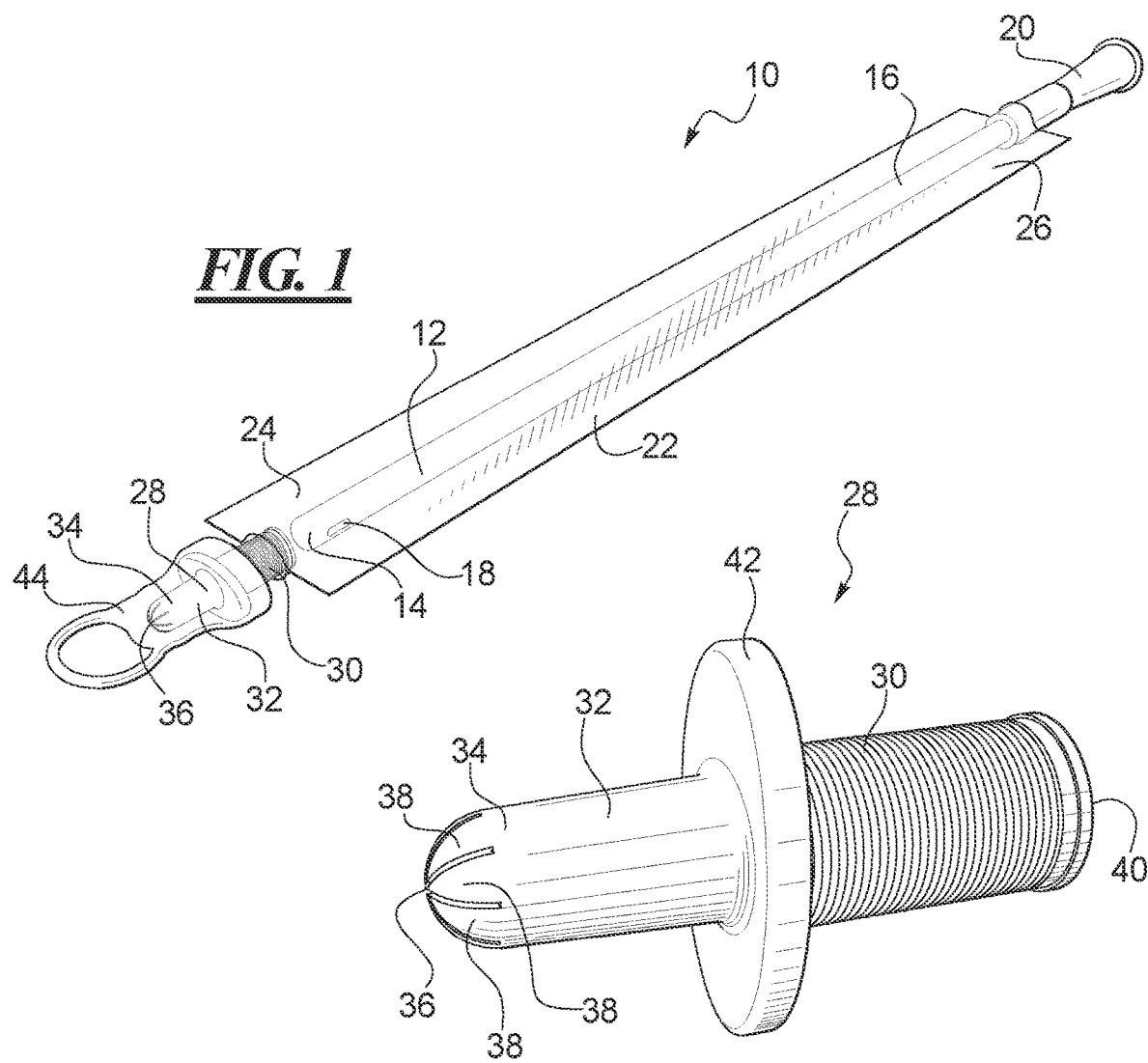
FIG. 1
FIG. 2
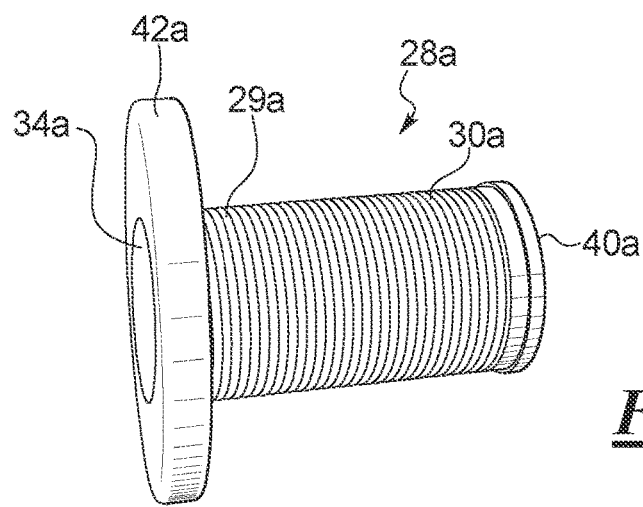
FIG. 3

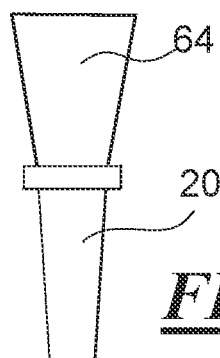
FIG. 5
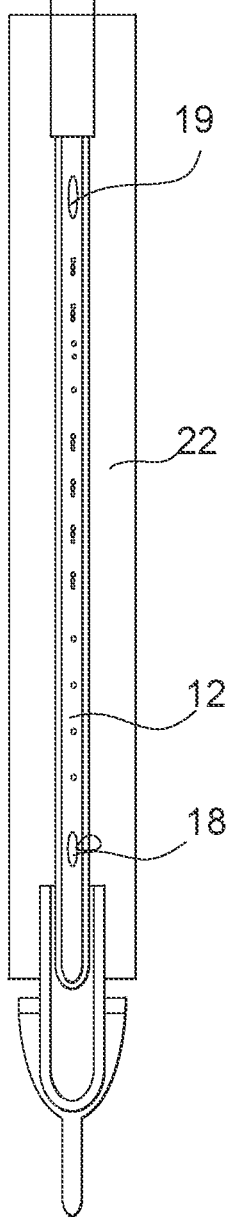
FIG. 6
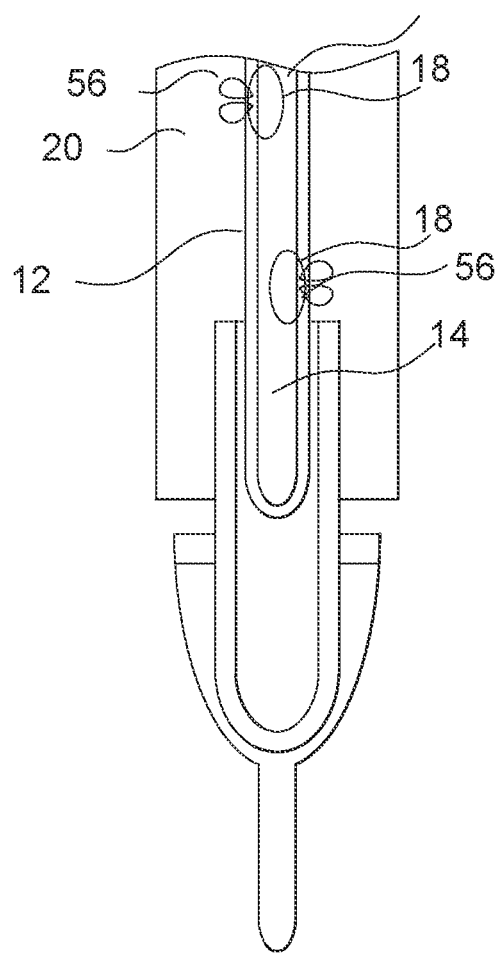

METHODS OF MAKING SLEEVED AND PACKAGED HYDROPHILIC CATHETER ASSEMBLIES

The present application is the U.S. National Stage Application of PCT Application No. PCT/US2020/059421, filed Nov. 6, 2020, which claims the benefit of and priority to U.S. Provisional Patent Application No. 62/932,979, filed Nov. 8, 2019, all of which is hereby incorporated herein by reference.

DESCRIPTION

Technical Field

The present disclosure generally relates to methods of making sleeved and/or packaged hydrophilic catheter assemblies wherein the catheter assemblies include a catheter tube that has an activated or hydrated hydrophilic outer surface and a barrier sleeve or package surrounds the catheter tube.

Background

It is known to coat medical devices, such as urinary catheters, with a hydrophilic coating. When the hydrophilic coating is wetted or hydrated with a hydration medium it becomes extremely lubricous. The hydration medium may be, for example, liquid or vapor water or an aqueous solution. The lubriciousness of the hydrophilic coating eases introduction of the device into the body and aids in reducing pain and discomfort associated with such introduction.

In some urinary catheter products, the user directly contacts the urinary catheter with the user's fingers to remove the catheter from the package and inserts it into the urethra. In such products there may be a disadvantage in that the handling of the catheter by the user may introduce microorganisms onto the surface of the catheter which can cause infectious problems after being introduced into the body during catheter insertion. To address this issue, manufacturers have devised systems that include a protective or barrier sleeve or package surrounding the catheter. In this type of product, the catheter tube is located in a barrier/package sleeve. The sleeve/package may loosely fit the diameter of the catheter so that the user may grasp the catheter tube through the sleeve to manipulate the catheter, e.g., advance the catheter into the urethra. In some products, the distal end of the sleeve may be attached to the drainage member of the catheter and an insertion aid may be attached to or otherwise associated with the proximal end of the sleeve.

One complication of employing a sleeve over a hydrophilic catheter is how to activate or hydrate the hydrophilic surface of the catheter located within the interior cavity of the sleeve.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method of making a urinary catheter product, wherein the product includes a sleeve defining an inner cavity and a urinary catheter having a catheter tube located within the inner cavity of the sleeve, the catheter tube having an outer hydrophilic surface, the method comprising delivering a hydration medium through the drainage member and an opening of the catheter tube into the interior cavity of the sleeve, wherein the hydration medium contacts the outer hydrophilic surface of the catheter tube.

In another aspect, a method of making a urinary catheter product, wherein the product includes a package defining an inner cavity and a urinary catheter having a catheter tube located within the inner cavity of the package, the catheter tube having an outer hydrophilic surface, the method comprising delivering a hydration medium through the drainage member and an opening of the catheter tube into the interior cavity of the package, wherein the hydration medium contacts the outer hydrophilic surface of the catheter tube within the package.

In another aspect, a system for delivering hydration medium into a catheter assembly. The system includes a source of hydration fluid and a nozzle in communication with the source of hydration fluid. The nozzle is configured to dock with a drainage member of a catheter assembly and deliver hydration fluid into the catheter assembly.

BRIEF DESCRIPTION OF FIGURES

FIG. 1 is a perspective view of a catheter assembly in accordance with the present disclosure;

FIG. 2 is a perspective view of one embodiment of an insertion aid of the assembly of FIG. 1;

FIG. 3 is a perspective view of another embodiment of an insertion aid of the assembly of FIG. 1;

FIGS. 5 and 6 are partial cross-sectional view showing the hydration medium being injected through the drainage member and into the cavity of the sleeve.

DETAILED DESCRIPTION OF THE ILLUSTRATED EMBODIMENTS

Figure 4:
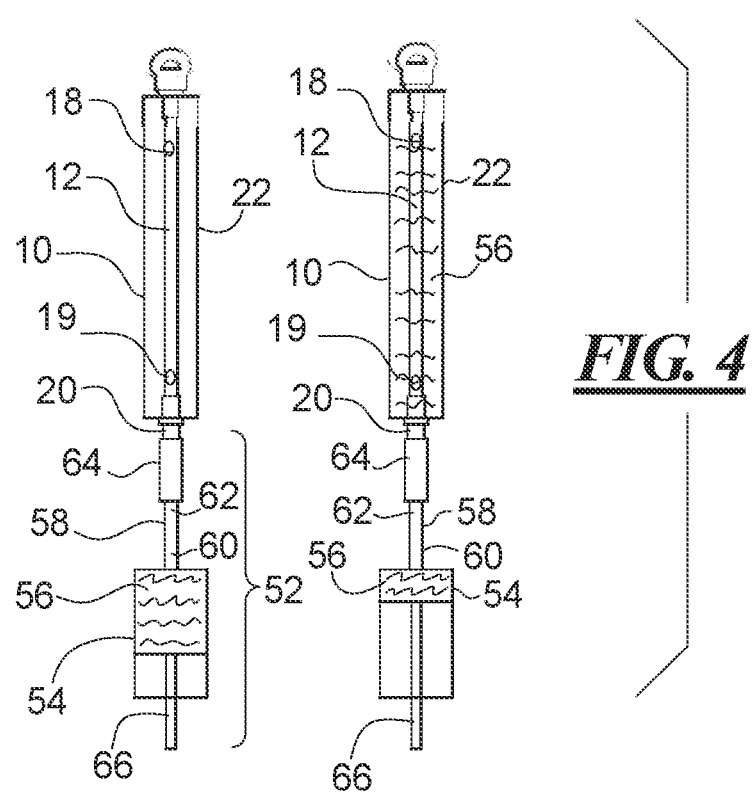
FIG. 4 is a schematic view of one embodiment of a method of making a hydrophilic sleeved catheter assembly and a hydration medium delivery device in accordance with the present disclosure.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to methods of making a sleeved or packaged hydrophilic urinary catheter product wherein the urinary catheter is ready-to-use right out of the outer package. That is, while in the package, the hydrophilic outer surface of the catheter tube within the interior cavity of the sleeve or package is in a hydrated/activated state, so that the catheter is ready-to-use right out of the package.

FIG. 1 illustrates one embodiment of a catheter assembly 10 in accordance with present disclosure. The catheter assembly 10 includes an elongated catheter tube 12 having a proximal end portion 14 and a distal end portion 16. The proximal end portion 14 of the catheter tube 12 is suitable for insertion into a lumen or a passageway of the body, such as the urethra. The proximal end portion 14 may include drainage holes or eyelets 18 for draining urine from the bladder. A drainage member 20 may be associated with the distal end portion 16 of the catheter tube 12. The catheter tube 12 includes an outer hydrophilic surface that becomes lubricious when hydrated or activated. The outer surface may be, for example, any suitable hydrophilic coating.

The catheter assembly 10 also includes a sleeve 22, which may be a protective or barrier sleeve that has a proximal end portion 24 and a distal end portion 26. The sleeve 22 surrounds at least a portion of the catheter tube 12 to separate and enclose the portion of the catheter tube 12 from the outside environment. In other words, the protective sleeve 22 defines an interior cavity in which the catheter tube 12 may be located. In one embodiment, the sleeve 22 extends over the length of the catheter tube 12. Optionally, an insertion aid 28 may be located at the proximal end portion 24 of the sleeve 22. When an insertion aid 28 is present, the proximal end portion 24 of the sleeve 22 may be attached to a barrel or stem 30 of the insertion aid 28, by for example, welding or adhesive. The distal end portion 26 of the sleeve 22 may be attached to the drainage member 20 or the distal end of the catheter tube 12. An insertion aid may be used with any of the catheter assemblies disclosed herein.

The sleeve 22 and any of the other sleeves disclosed herein may be made of a flexible material which may be vapor permeable or vapor impermeable, depending on the desired use and packaging. The material of the sleeve 22 may also be liquid impermeable. The sleeve 22 may be formed of any of a variety of thin, flexible polymeric film materials, such as polyethylene, plasticized PVC, or polypropylene, but elastomeric film materials such as polyurethane, and particularly elastomeric hydrogel materials, may be particularly suitable. The thickness of the film from which the sleeve 22 is formed may vary considerably depending on factors such as stretchability and flexibility of the material selected but, in general, the thickness may fall within the range of about 10 to 150 microns, preferably about 13 to 50 microns.

Referring to FIGS. 1, 2 and 3, these figures illustrate exemplary embodiments of the insertion aids. In FIGS. 1 and 2, the insertion aid 28 includes a proximal end portion 32 that defines an introducer tip 34. The introducer tip 34 has a proximal end aperture or opening 36 defined by one or more slits between one or more flexible petals 38. The petals 38 may move, bend and/or resiliently deform from the generally closed aperture configuration shown in FIGS. 1 and 2 to an open aperture configuration (not shown) to allow for advancement of the catheter tube 12 therethrough. The distal end portion of the insertion aid 28 includes a cylindrical or barrel portion 30 that has an opening 40 for receiving the catheter tube 12. The insertion aid 28 may also include an intermediate flange 42 that may contact the user about the urethra opening and act as a stop to limit the insertion of the introducer tip 34.

Turning to FIG. 3, in this embodiment the insertion aid 28a is a port 29a that includes a flange 42a surrounding an aperture or opening 34a. The catheter tube 12 advances through opening 34a for insertion into the urethra. The distal end portion of the port 29a includes a cylindrical or barrel portion 30a that has an opening 40a for receiving the catheter tube 12.

Turning back to FIG. 1, the insertion aid 28, optionally, may be covered by a removable protective cap 44. The removable protective cap 44 covers the insertion aid 28 and may protect the insertion aid 28 from contacting surfaces and objects prior to use.

To use the catheter assembly 10, the user opens and removes the catheter assembly 10 from an outer package (not shown). For example, the user opens the package and grasps the catheter tube 12 through the protective sleeve 22 to handle and manipulate the catheter assembly 10. The user removes protective cap 44, if one is present. If the catheter assembly 10 includes the insertion aid 28 shown in FIG. 2, then the user inserts the introducer tip 34 into the urethra. If the catheter assembly 10 includes the insertion aid 28a shown in FIG. 3, then the user aligns the opening 34a of the port 29a with the urethral opening. The user then grasps the catheter tube 12 through the sleeve 22 and advances the catheter tube 12 through the insertion aid 28/28a and into and through the urethra until the eyelets enter the bladder. If the catheter assembly 10 does not includes an insertion aid, then the user grasps the catheter tube 12 through the sleeve 22 and advances the tip of the catheter tube 12 out of the open end of the sleeve 22 and into the urethra. When the eyelets enter the bladder, urine flows through the eyelets and catheter tube 12 to drain the bladder.

In one method of making a sleeved hydrophilic catheter wherein the hydrophilic surface is in an activated or hydrated state, such as those described above, the method includes injecting or delivering a hydration medium into the interior cavity of the sleeve of the catheter assembly. While in the sleeve, the hydration medium contacts the hydrophilic surface of the catheter to at least partially hydrate or activate the hydrophilic surface, and in one embodiment, fully hydrates the hydrophilic surface. Optionally, the hydration medium dwells within the sleeve for a selected time period, which may be sufficient to partially or fully hydrate/activate the hydrophilic surface.

The hydration medium may be a liquid, foam or a gel. For example, the hydration medium may be liquid water or an aqueous solution or any other suitable liquid hydration medium. In one embodiment, the hydration medium may be an aqueous solution that includes water, glycerol and, optionally, other additives.

Optionally, the hydration medium may be a hydration foam that includes a liquid containing a mass of gas bubbles on or in the liquid. In one embodiment, the hydration foam medium includes, among other components, a liquid, a surfactant and gas. The liquid may be water or an aqueous solution. The surfactant may be any suitable foaming agent or surface tension reducing agent, such as sodium methyl cocoyl taurate, silicone surfactants or the like. The gas may be any suitable gas, such as ambient air, carbon dioxide, nitrogen, etc. The gas may be homogenized with the liquid to form a foam. When the hydration medium is a hydration foam, the hydration medium may be foamed and then delivered into the sleeve. Alternatively, the hydration medium may be foamed at the same time as it is delivered into the sleeve, or may be foamed after it is delivered into the sleeve.

In another embodiment, the hydration medium may be a water based gel. The gel based hydration medium may have a dual function, firstly hydrates hydrophilic coating and secondly protects retention of water. In one embodiment, the gel may be one that liquefies or becomes less viscous when exposed to radiation and may supplement hydration and lubriciousness of hydrophilic coating. For example, the gel may be a gellan gum based gel that is injected into the sleeve as a gel and then liquefies, breakdowns or becomes less viscous when the catheter assembly is exposed to sterilizing radiation, such as e-beam or gamma radiation. In one embodiment the gel may be a gel that includes 1.5 wt %-2 wt % of gellan gum, 1 wt % glycerol and 97 wt %-97.5 wt % of water.

The hydration medium (liquid or gel) may have an elevated temperature during injection into the interior cavity of the sleeve. For example, the hydration medium may be at a temperature between 15° C.-70° C. In another embodiment, the hydration medium may be at a temperature between 40° C.-70° C. during injection. Injecting the hydration medium at an elevated temperature may assist in the injection process. Additionally, injecting a hydration medium at an elevated temperature may lessen the time it takes for the hydration medium to hydrate/activate the hydrophilic surface of the catheter.

When the hydration medium is a gel, the gel may be injected into the sleeve as a hot gel solution at an elevated temperature, as discussed above. The hot gel solution may partially or substantially hydrate the hydrophilic coating of the catheter tube. Optionally, a selected amount of the hot gel solution may be withdrawn. Alternatively, the method may not include a withdrawal step. The gel in the sleeve or remaining in the sleeve after a withdrawal step may cool to ambient temperatures (e.g., about 23° C. or below). When the gel cools, it may form a thin gel coating, such as a hydrogel coating, at least partially covering, and preferably substantially covering, the partially or substantially hydrated hydrophilic surface of the catheter tube. Additionally, there may be surplus deposits of gel located within the sleeve. Such gel deposits may be gel that is in the sleeve but not covering the catheter. Depending on the gel used, the gel may not hydrate the hydrophilic surface of the catheter while in the gel state, at least partially hydrate the hydrophilic surface of the catheter while in the gel state, or fully hydrate the hydrophilic surface of the catheter while in the gel state. Furthermore, the gel may be a gel that liquefies or becomes less viscous when the catheter assembly is exposed to sterilizing radiation. For example, after the gel injection step and optional withdrawal step, the gel may be covering the hydrophilic surface of the catheter and/or may otherwise be located in the sleeve. The catheter assembly is then placed in a package. The package may then be exposed to sterilizing radiation wherein the gel liquefies or becomes less viscous.

Turning now to FIG. 4, this figure provides a schematic representation of a fill method that includes an injection system 52 for delivering hydration medium into the sleeve 22. The catheter assembly 10 may be docked or otherwise operatively connected to a hydration medium injection system or machine 52. The hydration medium injection and system 52 may include a source of hydration medium 54, which could be a reservoir or tank containing an amount of hydration medium 56. The system may include a conduit 58, one end 60 of which is connected to the source of hydration medium 54, and the end 62 of which is configured to be connected or docked to the catheter assembly 10 so that hydration medium 54 can be injected or delivered into the interior cavity of the sleeve 22. For example, the end 62 of the conduit 58 may include a nozzle 64 configured to be releasably connectable/docked to the drainage member 20. The system also includes a pump or metering valves or other element 66 for moving/pumping hydration medium 56 so as to inject hydration medium into the sleeve 22.

As discussed above, the method of forming the sleeved activated hydrophilic catheter may include, injecting a hydration medium into the interior cavity of the sleeve 22, wherein the hydration medium comes into contact with the outer hydrophilic surface of the catheter tube 12. Referring to FIGS. 4 and 5, there is shown and described one exemplary embodiment of forming the sleeved hydrophilic catheter shown in FIG. 1. The nozzle 64 of the injection system is docked or connected to the drainage member 20. It should be understood that catheter assembly 10 and the injection system 52 may be in any orientation. For example, in FIG. 4, the catheter assembly 10 and the injection system 52 are shown in an orientation wherein the hydration medium is injected upward through catheter 12, while in FIG. 5 the hydration medium is injected downward through the catheter 12.

The outer diameter of the nozzle 64 may have a size that generally corresponds to the inner diameter of the drainage member 20. After the nozzle 64 is dock, hydration medium 56 is injected from the nozzle 64 through the drainage member 20 and into the lumen of the catheter tube 12. Referring to FIGS. 4 and 6, the hydration medium 56 flows through the lumen and out of the eyelets 18 of the catheter tube 12 and into the sleeve 22 wherein the hydration medium contacts the hydrophilic surface of the catheter tube 12. Optionally, the catheter tube 12 may also include an opening/eyelet 19 near or proximate the drainage member 20 wherein hydration medium is delivered into the sleeve through this opening 19. As mentioned above, the hydration medium may be injected at an elevated temperature.

After the hydration medium 56 is injected into the sleeve, the catheter assembly 10 is then placed within an outer package (not shown) and the package is sealed. The outer package may then be submitted to sterilizing by e-beam or gamma radiation.

In one embodiment, the outer package may be made of a gas impermeable and liquid impermeable material, such as a polymer and aluminum laminate. Furthermore, the package may be of the type that has a vapor atmosphere or 100% relative humidity within the seal package. For example, the package may include therein a water compartment that is at least partial defined by a vapor permeable, liquid impermeable material. The water within the compartment may produce a water vapor that permeates through the vapor permeable, liquid impermeable material to create and/or maintain a hydration environment within the package. Additionally, when the catheter assembly is placed in a package having a vapor atmosphere, the sleeve may be vapor permeable to allow vapor to come into contact with the partially or substantially hydrated hydrophilic surface of the catheter tube. This may assist in maintaining the hydrophilic surface in an activated or hydrated state during storage and distribution. Alternatively, when the sleeve is made from a liquid and gas impermeable material and the interior cavity of the sleeve is sealed off, the outer package may be made from a gas permeable material.

Figure 7:
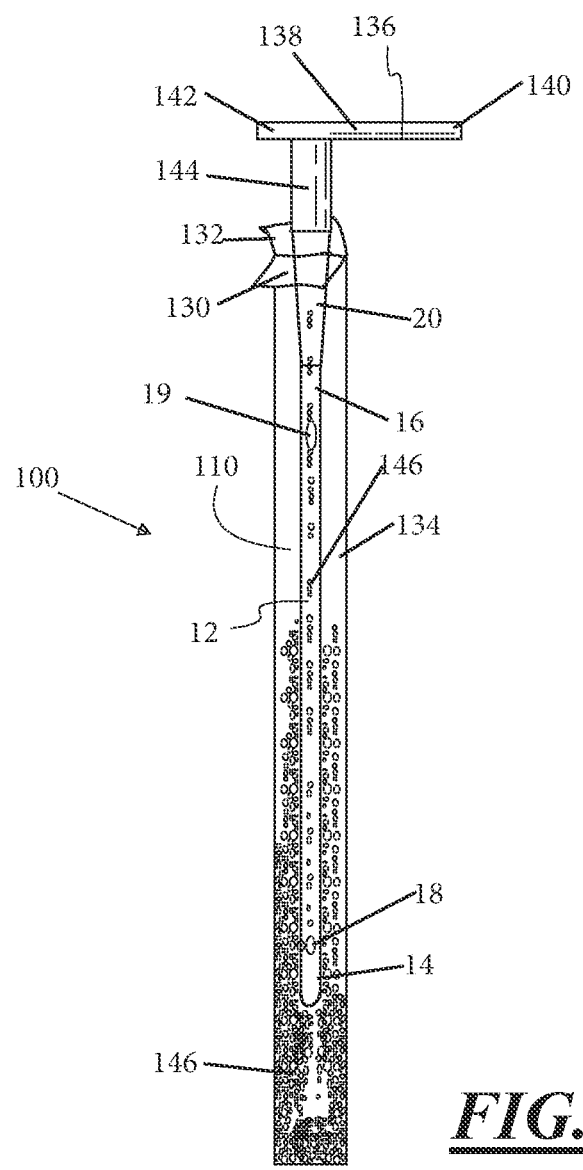
FIG. 7 is a side elevational view showing the hydration medium being injected through the drainage member and into the cavity of a package.

FIG. 7 illustrates another hydrophilic catheter product 100 and method of forming the same. The catheter product includes a package 110 and a catheter tube 12. The package 110 may be any suitable type of package. In the illustrated embodiment, the package includes a front sheet 130 and a rear sheet 132 that are sealed together about their peripheries. The package includes an internal cavity 134 that contains the catheter 12. The catheter 12 is similar to that described above. The catheter 12 includes a drainage member 20 associated with it distal end 16, and eyelets 18 associated with it proximal end 14.

The method of forming the catheter product 100 includes placing the catheter 12 within the package 110. The drainage member 20 is then docked or otherwise operatively connected to a hydration medium injection system or machine 136. The hydration medium injection and system 152 may include a source (not shown) of hydration medium, which could be a reservoir or tank containing an amount of hydration medium 156. The system 152 may include a conduit 138, one end 140 of which is connected to the source of hydration medium, and the end 142 of which is configured to be connected or docked to the drainage member 20. For example, the end 142 of the conduit 138 may include a nozzle 144 configured to be releasably connectable/docked to the drainage member 20.

After the nozzle 144 is dock, hydration medium 146 is injected from the nozzle 144 through the drainage member 20 and into the lumen of the catheter tube 12. The hydration medium 146 flows through the lumen and out of the eyelets 18 of the catheter tube 12 and into the interior 134 of the package 110 wherein the hydration medium 146 contacts the hydrophilic surface of the catheter tube 12. Optionally, the catheter tube 12 may also include an opening/eyelet 19 near or proximate the drainage member 20, wherein hydration medium 156 is delivered into the package through this opening 19.

After the hydration medium 56 is injected into the package, the package is sealed. The outer package may then be submitted to sterilizing by e-beam or gamma radiation.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A method of making a urinary catheter product, comprising:
    docking a drainage member of the urinary catheter product to a nozzle of a hydration medium delivery system, wherein the urinary catheter product includes a sleeve defining an inner cavity and a urinary catheter having a catheter tube located within the inner cavity of the sleeve, the catheter tube having an outer hydrophilic surface, and the drainage member being associated with the catheter tube;
    delivering a hydration medium from the nozzle through the drainage member and into the inner cavity of the sleeve, wherein the hydration medium contacts the outer hydrophilic surface of the catheter tube;
    undocking the nozzle from the drainage member;
    placing the sleeve and catheter in an outer package; and
    sealing the package.

2. The method of claim 1, wherein the catheter tube includes at least one eyelet and wherein the hydration medium flows through the catheter tube and out of the eyelet into the inner cavity of the sleeve.

3. The method of claim 2, wherein the eyelet is located in a proximal end portion of the catheter tube.

4. The method of claim 2, wherein the eyelet is located in a distal end portion of the catheter tube.

5. The method of claim 2, wherein a portion of the sleeve covers the eyelet.

6. The method of claim 1, wherein the hydration medium comprises a liquid.

7. The method of claim 1, wherein the hydration medium comprises a hydration foam.

8. The method of claim 1, wherein the hydration medium comprises a gel that releases a liquid.

9. A method of making a urinary catheter product, comprising:
    docking a drainage member of a urinary catheter product to a nozzle of a hydration medium delivery system, wherein the urinary catheter product includes a package defining an inner cavity and a urinary catheter having located within the inner cavity of the package, the catheter tube having an outer hydrophilic surface, and the drainage member being associated with the catheter tube;
    delivering a hydration medium through the drainage member and into the inner cavity of the package, wherein the hydration medium contacts the outer hydrophilic surface of the catheter tube;
    undocking the nozzle from the drainage member; and
    sealing the package, wherein the entire urinary catheter is located in the inner cavity of the package.

10. The method of claim 9, wherein the catheter tube includes at least one eyelet and wherein the hydration medium flows through the catheter tube and out of the eyelet into the inner cavity of the package.

11. The method of claim 10, wherein the eyelet is located in a proximal end portion of the catheter tube.

12. The method of claim 10, wherein the eyelet is located in a distal end portion of the catheter tube.

13. The method of claim 9, wherein the hydration medium comprises a liquid.

14. The method of claim 9, wherein the hydration medium comprises a hydration foam.

15. The method of claim 9, wherein the hydration medium comprises a gel that releases a liquid.

16. A system for delivering hydration medium into a catheter assembly, comprising:
    a hydration source comprising a reservoir containing a hydration fluid; and
    a nozzle in communication with the hydration source, the nozzle being configured to dock with drainage member of a catheter assembly and deliver the hydration fluid into the catheter assembly, wherein the nozzle is separate from the reservoir.

17. The system of claim 16, further including a pump for pumping the hydration fluid during delivery thereof.

18. The system of claim 16, further including a conduit, wherein the conduit includes a first end connected to the hydration source and a second end that includes the nozzle.

19. The system of claim 16, further including metering valves.

* * * * *